United States Patent [19]

Loewenthal et al.

[11] Patent Number: 4,886,454
[45] Date of Patent: Dec. 12, 1989

[54] DENTAL PROBE

[75] Inventors: Bernard Loewenthal, 51 Heights Rd., Stratham, N.H. 03885; G. Lawrence Thatcher, Chelmsford, Mass.

[73] Assignee: Bernard Loewenthal, Stratham, N.H.

[21] Appl. No.: 151,907

[22] Filed: Feb. 3, 1988

Related U.S. Application Data

[63] Continuation-in-part of Ser. No. 48,876, May 12, 1987, Pat. No. 4,768,952, which is a continuation-in-part of Ser. No. 937,409, Dec. 3, 1986, abandoned.

[51] Int. Cl.$^4$ ............................................. A61C 19/04
[52] U.S. Cl. ...................................... 433/72; 433/141
[58] Field of Search ................ 433/72, 75, 141, 147, 433/215; 33/513, 514

[56] References Cited

U.S. PATENT DOCUMENTS

| | | | |
|---|---|---|---|
| Re. 27,915 | 2/1974 | Kohl | 128/757 |
| 904,990 | 11/1908 | Powers | 433/147 |
| 1,586,302 | 5/1926 | Funk | 433/141 |
| 3,388,473 | 6/1968 | Loran | 433/75 |
| 3,411,723 | 11/1968 | Kohn | 433/141 |
| 3,855,705 | 12/1974 | Malmin | 433/72 |
| 3,935,640 | 2/1976 | Cohan | 433/75 |
| 4,203,223 | 5/1980 | Lautenschlager et al. | 433/141 |
| 4,340,069 | 7/1982 | Yeaple | 433/72 |
| 4,364,730 | 12/1982 | Axelsson | 433/147 |
| 4,377,381 | 3/1983 | Westman | 433/141 |
| 4,441,509 | 4/1984 | Kotsifas et al. | 128/757 |
| 4,445,857 | 5/1984 | Borst | 433/75 |
| 4,449,933 | 5/1984 | Forni | 433/141 |
| 4,501,555 | 2/1985 | Ditchburn | 433/72 |
| 4,552,531 | 11/1985 | Martin | 433/147 |

FOREIGN PATENT DOCUMENTS

| | | |
|---|---|---|
| 0119813 | 9/1984 | European Pat. Off. |
| 3411366 | 10/1985 | Fed. Rep. of Germany |
| 2230327 | 12/1974 | France |
| 2086232 | 12/1982 | United Kingdom |

OTHER PUBLICATIONS

Journal of Clinical Periodontology, "Microscopic Evaluation of Clinical Measurements of Connective Tissue Attachment Levels" Armitage et al, 1977, p. 175 Hu--Friedy Catalog, p. 4.

Primary Examiner—John J. Wilson
Attorney, Agent, or Firm—Foley & Lardner, Schwartz, Jeffery, Schwaab, Mack, Blumenthal & Evans

[57] ABSTRACT

A dental probe is disclosed for use in detecting periodontal disease and gingivitis. The probe includes an elongage member having a distal end with the double-tapered flexible plastic tip thereon; the distal end has a first portion indicating a non-diseased condition and a second portion indicating a diseased condition, the first portion being disposed between the tip of the distal end and the second portion, the second portion being disposed adjacent to the first portion. The invention also includes a method using the dental probe for diagnosing periodontal disease and gingivitis.

38 Claims, 2 Drawing Sheets

NORMAL

DISEASED

DENTAL PROBE

CROSS REFERENCE

This is a continuation-in-part of copending application Ser. No. 048,876, filed May 12, 1987 now U.S. Pat. No. 4,768,952, which is in turn a continuation-in-part of application Ser. No. 937,409, filed Dec. 3, 1986 now abandoned. These prior applications are incorporated by reference.

BACKGROUND OF THE INVENTION

1. Field of the Invention

This invention relates to a periodontal probe. In particular, this invention relates to a flexible tip periodontal probe having a calibrated tip for diagnosing periodontal disease and gingivitis.

2. Description of the Related Art

Periodontal disease is the most widespread disease in the world. It is basically an inflammatory disease of the gums which spreads to and destroys the supporting bone of the teeth. In time, teeth may abscess, become loose or painful and either fall out or are removed by a dentist. Periodontal disease is by far the major cause of tooth lose in the adult population. Fortunately, the dental profession has continually developed more effective methods to treat periodontal disease. However, the success of these treatments is greatly dependent upon early detection, usually by a dentist.

The disease is frequently silent as characterized by an absence of symptoms, much like high blood pressure. For example, there may or may not be bleeding or pus around the teeth. Advanced cases frequently cause systemic problems due to the massive amount of infection that can be present.

The sole cause of periodontal disease is dental plaque which is a bacterial substance present on teeth. However, due to the fact that every person has a different genetic background, some people are resistant to the disease while others are extremely prone. Additionally, the problem is enhanced by infrequent dental visits and non-diagnosis of the disease.

The periodontal probe is the only significant clinical tool used for checking a person's periodontal disease status. The conventional periodontal probe is inflexible, made of metal and available only to dentists for professional use. These conventional probes have either lines or marks to indicate the depth that the probe penetrates between the tooth and the gum. A non-diseased condition is reflected by a probe depth of from 1 to 3 millimeters between the tooth and gum. A deeper insertion indicates a problem and the depth of the insertion corresponds to the amount of bone loss.

Because of the inflexibility of the standard metal probe, the tip cannot bend. Thus, the tip of the probe goes through the wall of pockets of periodontal tissues, thus causing pain discomfort and inaccurate measurements. Lacking a flexible tip periodontal probe, dentists occasionally insert a flexible gutta percha point into periodontal pockets and take a radiograph to see the anatomy of the pocket, since gutta percha can be visualized on x-ray. This procedure is obviously very tedious and exposes the patient to additional x-rays and expense.

A primary or first stage of periodontal disease is gingivitis which is detected by eliciting any bleeding while probing. One method of diagnosis of gingivitis is the use of pieces of balsa wood which are sold, for example, by Johnson & Johnson under the trademark "STIM-U-DENT." One problem with the use of pieces of balsa wood is that they are too large and rough to be used accurately.

It has been difficult or impossible to reach into periodontal pockets because they are tortuous, and the metal probes can only go in a straight line and may not penetrate the full depth of the pocket.

Further, many back teeth have two or more roots. Frequently, bone is lost during periodontal disease between the roots. This area of the tooth where the roots divide is referred to as the "furcation." When bone is lost between roots, there exists a "furcation involvement." The depth of furcation involvement is of paramount importance in determining the prognosis and treatment of the tooth. Without a means of properly penetrating these areas, it is difficult or impossible to make a proper diagnosis.

A majority of dentists do not routinely probe for periodontal disease. In addition to the lack of routine examination by the dental profession, most physicians are not even aware of the problem.

Present reusable probes can produce situations which cause concern both for dentists and patients, particularly with the advent of acquired immunity deficiency syndrome (AIDS).

The dental instrument art lacks a probe that the consumer can use to self-diagnose periodontal disease and gingivitis. The medical profession also lacks a disposable, easy-to-use dental probe for detecting periodontal disease and gingivitis. A method for routinely diagnosing and monitoring periodontal disease and gingivitis by persons other than a dentist does not currently exist.

SUMMARY OF THE INVENTION

It is therefore an object of the present invention to provide a dental probe useful for the early detection of periodontal disease and gingivitis.

It is also an object of the present invention to provide a dental probe that allows for inexpensive self-testing at home.

It is a further object of the present invention to provide an opportunity to educate the user about periodontal disease.

Another object of the invention is to provide a flexible tip periodontal probe which can "snake" its way around tortuous pockets and give a more reliable diagnosis of periodontal disease.

A further object is to provide a flexible tip periodontal probe which is able to bend and not pierce the wall of pockets caused by the disease.

Another object is to detect furcation involvement by means of a flexible tip periodontal probe which has the ability to flex and bend equally in all directions, thus enabling the examiner to probe furcations in a manner not previously possible, specifically because conventional probes are rigid and cannot negotiate furcations.

Another object is to provide a flexible rounded tip probe which is more comfortable to use than conventional rigid probes. The flexible tip of the instant invention does not penetrate the wall of the pocket formed by gum tissue as is the case with the rigid conventional probe. This eliminates much of the pain since it bends, making the examination more comfortable.

Another object of the invention is for research purposes in demonstrating the position of the tip of the periodontal probe when in use which could not previously be done because the metal probe could not be cut along with the bone and gum tissue due to its hardness.

Yet another object is the diagnosis of gingivitis by demonstrating the bleeding point.

Still another object of the invention is the use of a flexible tip plastic probe in determining the periodontal status around titanium screw implants. This is because it is recommended that such implants not be touched by metal or anything that could scratch them. Any scratches on implants will attract plaque and may affect the prognosis.

Another object of the invention is to provide an easy to use, disposable periodontal probe for the use of dentists and physicians to routinely check for periodontal disease.

It is still another object of the invention to provide a method for the detection of periodontal disease.

Yet another object of the invention is to provide a dental probe, while disposable, may also be reusable by consumers or professionals, for the detection of periodontal disease that does not require a visit to the dentist unless a problem is indicated by the use of the periodontal probe.

In accordance with one aspect of the present invention these objects are achieved by a flexible tip plastic dental probe, comprising:

an enlongated member having a flexible, plastic distal end with a flexible tip thereon;

the distal end comprising a first portion indicating a non-diseased condition and a second portion indicating a diseased condition;

wherein the first portion is disposed between the tip of the distal end and the second portion, and the second portion is disposed adjacent to the first portion.

In accordance with another aspect of the present invention these objects are achieved by a method for diagnosing periodontal disease comprising the steps of:

(a) retracting the lip of a person to be diagnosed;

(b) gently inserting a dental probe, at the juncture between a tooth and gum, comprising:

an elongated member having a flexible, plastic distal end with a tip thereon;

the distal end comprising a first portion indicating a non-diseased condition and the second portion indicating a diseased condition;

wherein the first portion is disposed between the tip of the distal end and the second portion, and the second portion is disposed adjacent to the first portion;

(c) examining the distal end and ascertaining which of the two portions is visible at the juncture;

(d) removing the dental probe from between the tooth and gum; and (e) repeating steps (b) through (d) at least once.

A specific probe found most useful has a double taper in the tip area, allowing a small diameter very flexible tip for ease of insertion between the tooth and the gum, while providing a higher moment of inertia for stiffness adequate for probing. This cylindrical double taper tip design allows flexibility throughout a full hemisphere in the distal portion of the tip while maintaining probing stiffness. At the same time, a flexible plastic probe tip is provided which may include talcum, mica or fiberglass filler which can produce proper strength while maintaining flexibility in the tip region.

BRIEF DESCRIPTION OF THE DRAWINGS

Other objects, features and advantages of the present invention will become apparent from the following detailed description and accompanying drawings wherein.

DETAILED DESCRIPTION OF THE PREFERRED EMBODIMENTS

Figure 1:
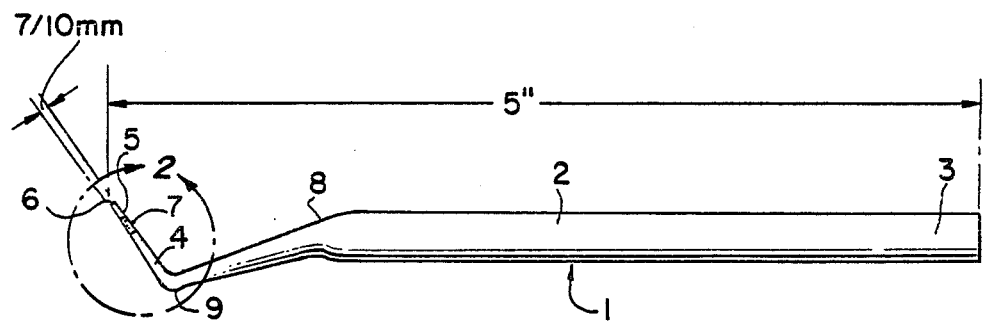
FIG. 1 is a side plan view of a dental probe.

Referring to FIG. 1, there is shown a dental probe 1 comprising an elongated member 2. The elongated member 2, which is of FDA compliant non-toxic white plastic material suitable for oral use, has a proximal end 3 and a distal end 4. Such material can be polypropylene homopolymer, polypropylene co-polymer, high density polyethylene homo polymer or polyethylene co-polymer or polybutylene terephthalate or nylon or ABS (acrylonitrile, butadiene, styrene, ter polymer) or acrylic multipolymer, or polymer blends or alloys; which may incorporate a 5% to 45% talcum, mica or fiberglass filler. In the preferred embodiment the material is either 40% talcum filled polypropylene homo polymer or polybutylene terephthalate, with filled polypropylene homo polymer being the preferred of the two. In order to obtain the desired flexibility, material is used which has a flex modulus (tangent) in the range of about $1.3-9.2 \times 10^5$ p.s.i. with a preferred modulus of about $5.1 \times 10^5$ p.s.i.

The distal end 4, which is flexible, has a first portion 5, indicating a non-diseased condition, which is disposed between a tip 6 and a second portion 7. The second portion 7 indicates a diseased condition and is disposed adjacent to the first portion 5.

The elongated member 2 has a first bend 8 disposed between the proximal end 3 and the distal end 4. A second bend 9 is disposed between the tip 6 and the first bend 8. It should be noted that the elongated member can have any number of bends at any desired angle which can achieve the desired function of enabling the dental probe to be held by hand and enabling the easy insertion of the distal end at the juncture between a tooth and gum. The purpose of the bends in the elongated member is to offset the distal end at an angle which facilitates easy insertion and examination of the dental probe. A desired embodiment is achieved when the first bend is directed downward forming an obtuse angle at the bottom side of the elongated member and the second bend is directed upward forming an obtuse angle at the top side of the elongated member.

Figure 2:
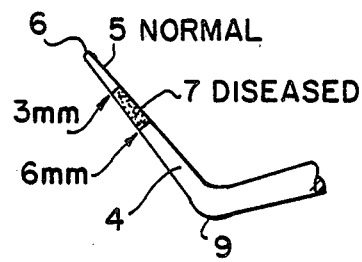
FIG. 2 is a magnified view of a section of the distal end of the dental probe shown in Figure.

Referring to FIG. 2 there is shown a magnified view of a section of the flexible distal end of the dental probe shown in FIG. 1 in which the first portion 5 is about 3 millimeters in length and the second portion 7 is about 3 millimeters in length, both portions together extending a length of about 6 millimeters from the tip 6. When the distal end is inserted at the juncture between a tooth and gum up to a length of about 3 millimeters, the first portion remains visible indicating a non-diseased condition. Insertion of the distal end beyond about 3 millimeters results in the second portion only being visible indicating a diseased condition. FIG. 2 shows the second portion extending from about the 3 millimeter mark to about the 6 millimeter mark; in a further embodiment the second portion can extend beyond about the 6 millimeter mark due to the fact that any insertion over about 3 millimeters indicates a diseased condition.

Additionally, the first and second portions can be contrastingly color-coded to aid the user when attempting to ascertain which of the two portions is visible during the examination. In one example of color-coding, the first portion can be colored green and the second portion can be colored red. In effect, any two colors which contrast each other can be chosen. The color is obtained by the use of a non-toxic compliant ink.

The dental probe shown in FIG. 1 is about 5 inches in length, but can be any length that is convenient for hand-held use. The dental probe shown in FIG. 2 tapers from the first bend 8 to the tip 6 which has a width of about 5/10 of a millimeter. The tip at the distal end can have any width that is suitable for inserting the distal end at the juncture between a tooth and gum. The probe is flexible or bendable from point 11 to tip 6 in order to achieve the objects discussed above.

Figure 5:
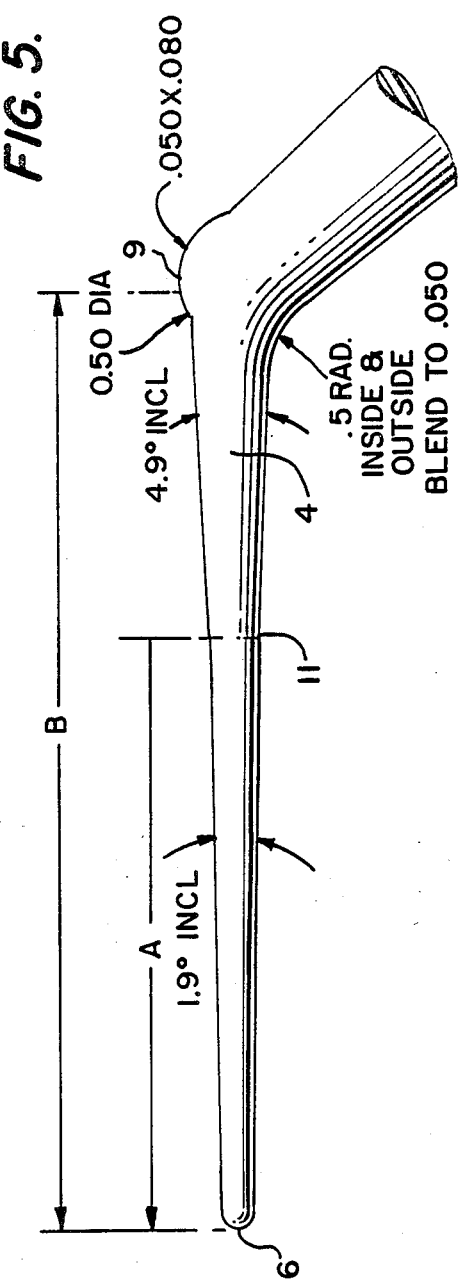
FIG. 5 is a further enlarged and dimensional view of the tip.

Referring to FIG. 5, the proximal end 3 of the elongated member 2 has a generally cylindrical shape. The preferred embodiment includes a tip which includes a double taper. A tip end 6 has a diameter of about 0.020 inches, as opposed to the usual metal probe of about 0.030 inches.

By making the probe in this fashion a smaller diameter tip can be used more comfortably than with metal, because a thin metal probe can pierce the wall of the periodontal pocket and cause pain. In other words, a thin metal probe can be too sharp. The probe tip is designed to taper for a distance and at an angle of between about 1° and 5+ with a preferred angle of about 1.9° to a point 11, which in the preferred embodiment is about 1 cm or about 0.4 inches. At point 11 the diameter increases to about 0.030 inches. It has been estimated that the diameters at points 6 and 11 might vary from about 0.010–0.015 at point 6 to about 0.040 at point 11. However, the diameters of 0.020 and 0.030 inches are presently the preferred embodiment.

The diameter of the tip then enlarges at a rate of about 3° to 8° with a preferred angle of about 4.9° to point 9 where the diameter is about 0.050 inches and can have the configuration and dimension seen in FIG. 5. However, the criticality of these latter dimensions are obviously not as significant. The distance from point 6 to point 9 indicated as B is about 4 cm or about 0.625 inches. It has been found that if the taper were constant, e.g., 1.9+ for the entire length, the strength or stiffness would be inadequate. The double taper provides a higher moment of inertia in region 4, than a taper constant from the tip, thus providing greater stiffness with a material of a given flex modulus. The double taper provides a means to deliver a filled material to the tip with reduced segregation, providing a uniform flex modulus throughout the tip. The double taper also provides a means to channel or direct polymer molecules orientation and, as indicated, filler orientation for optimum properties.

The present invention also includes a method for diagnosing periodontal disease. This method includes the steps of retracting the lip, cheek and or tongue of a person to be diagnosed and gently inserting a dental probe at the juncture between a tooth and gum. The distal end is then examined to ascertain which of the two portions is visible at the juncture and ultimately whether a diseased or non-diseased condition exists.

This method creates a simple yes-no situation. The dental probe is then removed from between the tooth and gum and gently inserted at another juncture. This process can be repeated until all the tooth/gum junctures are examined, or until only troubled areas are examined, if desired.

Figure 3:
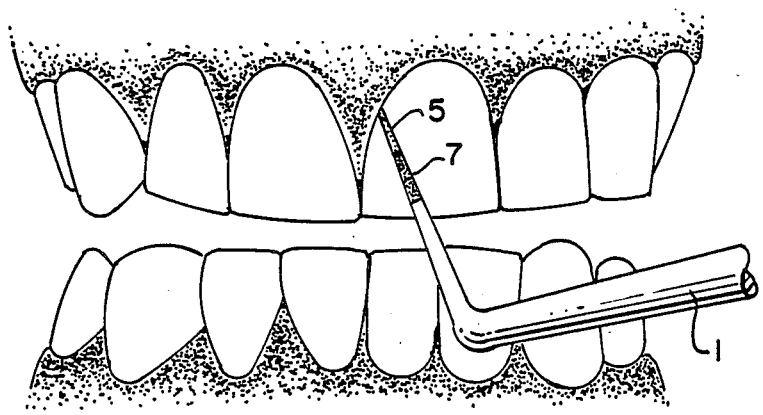
FIG. 3 is a perspective view of a dental probe inserted at the juncture between a healthy tooth and gum.

Referring to FIG. 3, there is shown the dental probe 1 inserted at a juncture between a tooth and gum. The first portion 5 remains visible indicating a non-diseased condition. The second portion 7 is also visible as a result of the dental probe not being able to penetrate at least about 3 millimeters.

Figure 4:
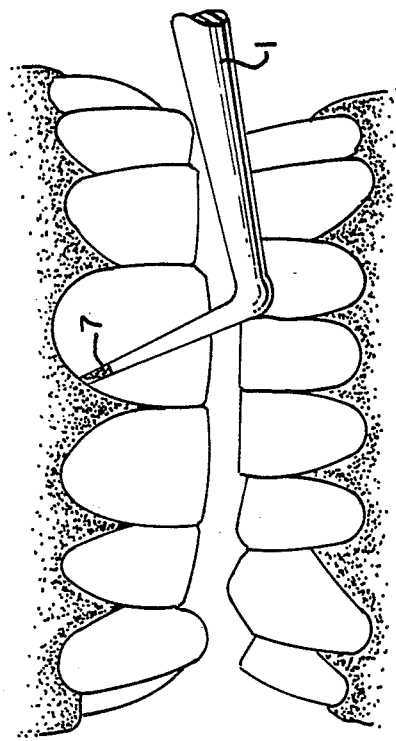
FIG. 4 is a perspective view of a dental probe inserted at the juncture between a diseased tooth and gum.

Referring to FIG. 4, there is shown the dental probe 1 inserted at a juncture between a tooth and gum in which only the second portion 7 remains visible indicating a diseased condition.

The method of detecting gingivitis is substantially the same in that the probe is used to detect any bleeding. Since the tip is flexible, it can go around corners in tortuous pockets and the examiner can ascertain the full depth of the pockets. The probe can also be used to ascertain furcation involvement.

The present method can also include the step of coding the two portions with contrasting colors for ease of identification. The specific portion of the distal end visible for each tooth and gum area examined can be charted with an examination chart showing the teeth and gums in their position relative to one another. In this method, the entire mouth can be charted to determine where the troubled spots are. Additionally, the chart can be used to indicate whether or not bleeding occurred. Therefore, at a glance, the patient can see from the chart where the pockets are or where bleeding occurred. A person using this method can conceivably chart themselves after a period of time to see what changes may have occurred following either professional care or self-treatment, for example, by improved tooth brushing and dental flossing. The probe as stated above, can be made from plastic and can be disposable, depending upon the desired use.

While several embodiments of the invention have been described, it will be understood that it is capable of still further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A dental probe comprising:
   (a) an elongated member having a flexible plastic distal end with a tip thereon; and
   (b) said distal end comprising a pair of different substantially cylindrical tapered portions thereon, the rate of tapering of one portion being different from the rate of tapering of the other portion whereby the probe end achieves the proper strength and flexibility.

2. The dental probe according to claim 1 wherein:
   said distal end comprises a first portion indicating a non-diseased condition and a second portion indicating a diseased condition; and
   said first portion disposed between the tip of said distal end and said second portion, said second portion disposed adjacent to said first portion.

3. The dental probe according to claim 2, wherein said first portion is about 3 millimeters in length and said second portion is at least about 3 millimeters in length.

4. The dental probe according to claim 2, wherein said first portion and said second portion are contrastingly color coded.

5. The dental probe according to claim 4, wherein said first portion is green and said second portion is red.

6. The dental probe according to claim 1, wherein said probe is disposable.

7. The dental probe according to claim 1, wherein at least said probe tip is plastic containing a filler selected from a group consisting of talcum, mica and fiberglass.

8. The dental probe according to claim 7, wherein said filler comprises between about 5% to 45% of said plastic.

9. The dental probe according to claim 1, wherein said plastic is selected from a group consisting of polypropylene homo-polymer and polybutylene terephthalate.

10. A dental probe according to claim 1, wherein said plastic is selected from a group consisting of polypropylene homo-polymer, polypropylene co-polymer, high density polyethylene homo-polymer, polyethylene co-polymer, polybutylene terephthalate, nylon or ABS (acrylonitrile, butadiene, styrene, ter polymer) and acrylic multipolymer.

11. A dental probe according to claim 10 including a filler selected from the groups consisting of talcum, mica and fiberglass.

12. A dental probe according to claim 1, wherein said plastic is polypropylene homo-polymer containing a talcum filler.

13. A dental probe according to claim 12, wherein said filler is about 40%.

14. A dental probe according to claim 1, wherein said plastic has a flex modulus (tangent) of about $1.3-9.2 \times 10^5$ p.s.i.

15. A dental probe according to claim 1, wherein said plastic has a flex modulus (tangent) of about $5.1 \times 10^5$ p.s.i.

16. The dental probe according to claim 1, wherein said elongated member has a first bend disposed between a proximate end and a distal end.

17. The dental probe according to claim 16, wherein said distal end has a second bend disposed between said distal end tip and said first bend.

18. The dental probe according to claim 17, wherein said first bend forms an obtuse angle at a bottom side of said elongated member.

19. The dental probe according to claim 17, wherein said second bend forms an obtuse angle at a top side of said elongated member.

20. The dental probe according to claim 1, wherein a first taper from said distal end is between about 1° to 5° and a second taper is between about 3° and 8°.

21. The dental probe according to claim 1, wherein a first taper from said distal end is about 1.9° and a second taper is about 4.9°.

22. The dental probe of claim 1 wherein said distal end includes a double taper, a first taper having a diameter of between about 0.010 to 0.020 inch to about 0.030 to 0.040 inch at an angle of about 1.9° from said tip for a distance of about 1 cm, and a second taper having a diameter from between about 0.020 to 0.040 inch are extending at an angle of about 4.9°.

23. A method for diagnosing periodontal disease comprising the steps of:
(a) retracting the lip of a person to be diagnosed;
(b) gently inserting a dental probe, at a juncture between a tooth and gum, comprising:
an elongated member having a double-tapered flexible, plastic distal end with a tip thereon, the rate of tapering of one portion being different from the rate of tapering of the other portion whereby the probe end achieves the proper strength and flexibility;
said distal end comprising a first portion indicating a non-diseased condition and second portion indicating a diseased condition; and
said first portion disposed between the tip of said distal end and said second portion, said second portion disposed adjacent to said first portion;
(c) examining said distal end and ascertaining which of said two portions is visible at the juncture;
(d) removing said dental probe from between the tooth and gum; and
(e) repeating steps b through d at least once.

24. The method according to claim 23 further comprising the step of coding said two portions with contrasting colors.

25. The method according to claim 23 further comprising the step of charting the specific portion visible for each tooth and gum area examined.

26. The method according to claim 23 including bending said tip in tortuous pockets.

27. The method according to claim 23 including locating furcation involvement.

28. The method according to claim 23 including forming at least said tip of a talcum filled polypropylene homo-polymer.

29. The method according to claim 23 including forming at least said tip of a polybutylene terephthalate.

30. The method according to claim 23 including forming a first taper from the tip at an angle of between about 1° to 5° for a first distance and then a second taper at an angle of between about 3° to 8°.

31. The method according to claim 23 including forming a first taper from the tip at an angle of about 1.9° for a distance of about 1 cm and then at a second taper at an angle of about 4.9°.

32. The method of claim 23 including forming the tip with a substantially cylindrical diameter of about 0.020 inch for a distance of about 1 cm to a diameter of about 0.030 inch.

33. The method of claim 23 including forming the tip with a plastic having a flex modulus (tangent) of about $1.3-9.2 \times 10^5$ p.s.i.

34. The method of claim 23 including forming the tip with a plastic having a flex modulus (tangent) of about $5.1 \times 10^5$ p.s.i.

35. A methid of diagnosing periodontal disease, comprising:
(a) forming a dental probe with an enlongated member having a distal end with a double-tapered flexible plastic tip thereon, the rate of tapering of one portion being different from the rate of tapering of the other portion whereby the probe end achieves the proper strength and flexibility, and
(b) probing the distal end at a juncture between a tooth and gum.

36. The method of claim 35 including eliciting any bleeding while probing to diagnose gingivitis.

37. The method of claim 35 including bending the tip around corners in tortuous pockets.

38. The method of claim 35 including bending the tip into furcations to diagnose furcation involvement.

* * * * *